United States Patent [19]
Marsh et al.

[11] 4,050,016
[45] Sept. 20, 1977

[54] VOLUMETRIC MOISTURE TESTER

[75] Inventors: Norman F. Marsh, Auburn; Warren H. Kelly, Springfield, both of Ill.

[73] Assignee: Dickey-john Corporation, Auburn, Ill.

[21] Appl. No.: 673,195

[22] Filed: Apr. 2, 1976

[51] Int. Cl.² ............................................. G01R 27/26
[52] U.S. Cl. .................................................. 324/61 R
[58] Field of Search ................ 324/61 R, 61 P, 65 R, 324/65 P

[56] References Cited

U.S. PATENT DOCUMENTS

| | | | |
|---|---|---|---|
| 2,759,147 | 8/1956 | Stein | 324/61 P |
| 2,774,938 | 12/1956 | Edinborgh | 324/61 R |
| 2,825,870 | 3/1958 | Hart | 324/61 R X |
| 2,947,940 | 8/1960 | Stein | 324/61 R X |
| 3,081,429 | 3/1963 | Moe | 324/61 R |
| 3,376,503 | 4/1968 | Lundstrom | 324/61 R |
| 3,559,052 | 1/1971 | Fathauer | 324/61 R |
| 3,566,260 | 2/1971 | Johnston | 324/61 R |
| 3,760,267 | 9/1973 | Williams | 324/61 R |

*Primary Examiner*—Stanley T. Krawczewicz
*Attorney, Agent, or Firm*—Olson, Trexler, Wolters, Bushnell & Fosse, Ltd.

[57] ABSTRACT

A moisture tester for grain and like materials is disclosed. The tester includes a walled test chamber including spaced apart electrodes which form an electrical coaxial capacitor, the electrodes being located so that the dielectric constant of the capacitor is modified in accordance with the dielectric constant of a test material sample introduced into the test chamber. To limit the volume, and to configure and pack the volume of test material introduced into the tester in a predetermined way, a funnel arrangement is provided at the tester top. A lower portion of the funnel directs inflowing grain over an axially aligned, centrally located finger which forms one of the electrodes. A pour spout is provided for pouring test sample material from the test chamber after test completion.

6 Claims, 3 Drawing Figures

VOLUMETRIC MOISTURE TESTER

BACKGROUND OF THE INVENTION

This invention relates generally to moisture testing apparatus, and more particularly concerns a device for testing the moisture content of grains.

Determining the moisture content of grains by sampling methods is an important activity in modern agriculture. One grain sample moisture testing device which has met with commercial success is that disclosed and claimed in U.S. Pat. No. 3,794,911. In this device, a sample of grain is introduced into a test chamber and is weighed, and data corresponding to the moisture content of the grain is visually displayed upon a suitable screen.

It is a general object of the present invention to provide a moisture tester for grain and the like which is highly reliable and rugged in operation, yet which provides data sufficiently reproducible and accurate for many important uses. Among these uses are the discernment of trends in moisture variations when a series of samples are compared.

Another object is to provide a moisture tester into which a fixed volume of test material is introduced into the test cell, and is packed into the test cell in a preordered, uniform manner. The tester itself is calibrated to give a relatively accurate reading of moisture on a percent of total sample weight basis.

Another object of the invention is to provide such a moisture tester which can be offered at low cost to the marketplace.

Yet another object is to provide such a device which can be used by even inexperienced personnel and which will nevertheless provide reliable, reproducible results within an acceptable range of error.

Other objects and advantages of the invention will become apparent upon reading the following detailed description and upon reference to the drawings. Throughout the drawings, like reference numerals refer to like parts.

DETAILED DESCRIPTION

While the invention will be described in connection with a preferred embodiment, it will be understood that it is not intended to limit the invention to this embodiment. On the contrary, it is intended to cover all alternatives, modifications and equivalents as may be included within the spirit and scope of the invention as defined by the appended claims.

Figure 1:
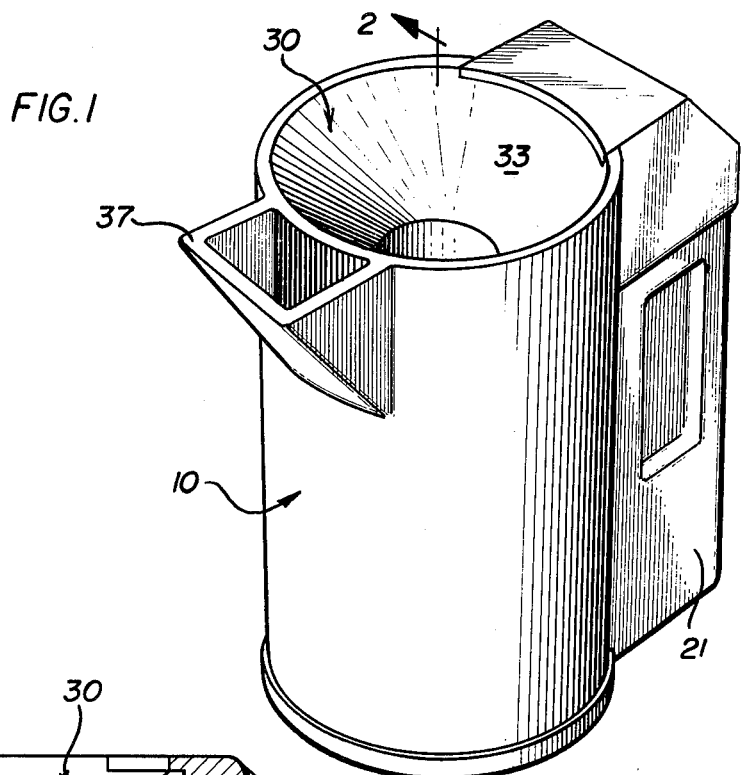
FIG. 1 is a perspective view showing a novel moisture tester apparatus as it appears in its general aspect.
Figure 2:
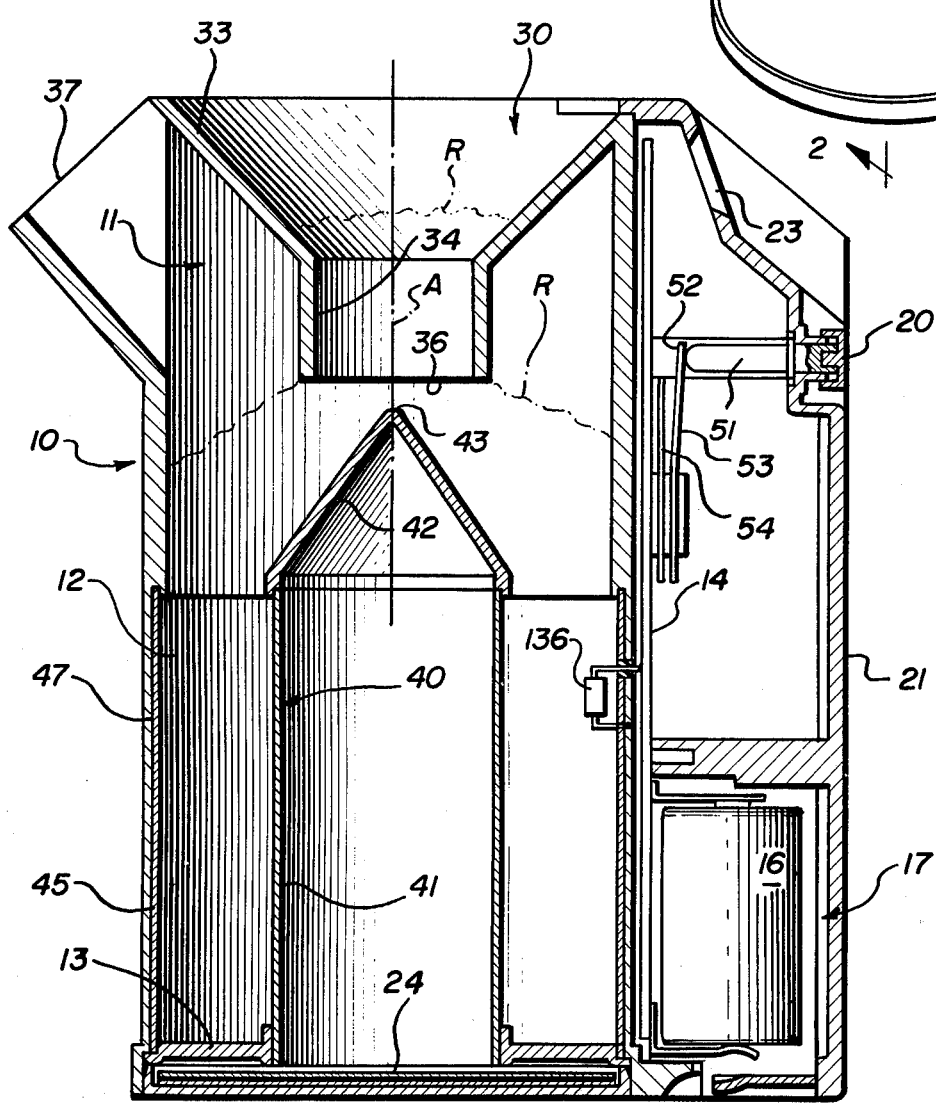
FIG. 2 is a sectional view taken substantially in the plane of line 2—2 in FIG. 1 and showing interior details of the device.
Figure 3:
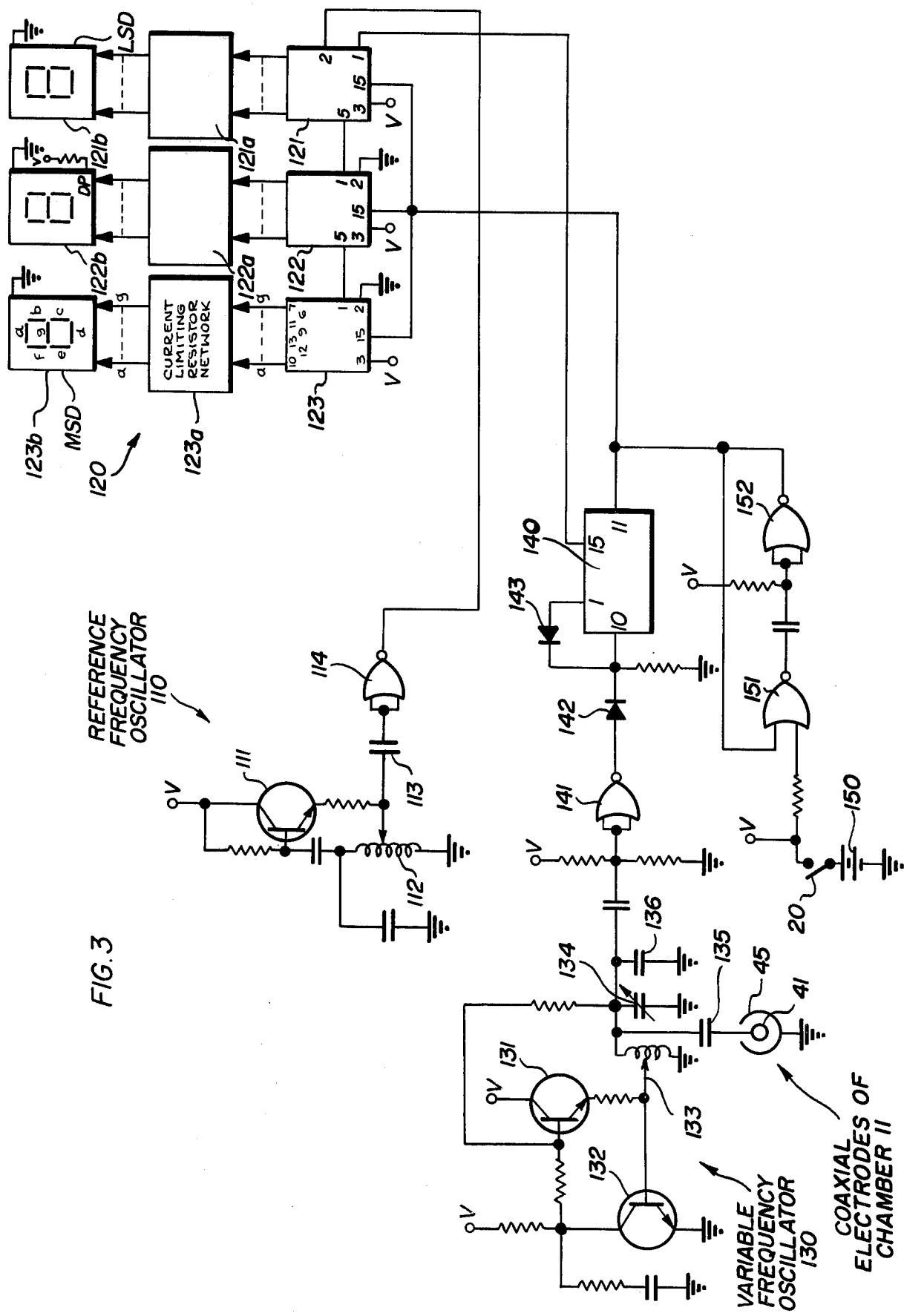
FIG. 3 is a schematic diagram of an electrical circuit which can be provided in the novel apparatus.

Turning first to FIGS. 1 and 2, there is shown a moisture tester device 10 which embodies the present invention and is adapted for use with grains such as corn and the like. In general, this device 10 includes a test chamber 11 which is defined by a cylindrical wall 12 and an annular bottom 13. Electrical components described below with respect to FIG. 3 are interconnected in an electrical circuit constructed upon a circuit board 14 which is here mounted on the side of the test chamber 11. This circuit is powered by a battery 16 carried in a battery housing 17. To conveniently operate the device, a circuit-energizing thumb switch 20 is mounted immediately above a hand or finger-accommodating handle 21 in a position which permits the tester 10 to be held and the switch 20 to be operated by one hand. Data relating to the moisture content of any grain sample contained within the test chamber 11 is displayed on a display screen 23 which is here conveniently mounted above the actuator switch 20. To minimize test chamber end capacitance leakage, a grounded metal capacitance shield plate 24 is affixed in the device bottom.

Atop the test chamber 11, a funnel device 30 is formed. In the illustrated device, this funnel 30 includes an upper portion 33 extending outwardly and upwardly from the remaining portions of the tester 11, and a lower portion 34 terminating in a lower margin 36 which is located at a fixed position relative to the test chamber.

In operation, a quantity of grain or other granular substance to be tested for moisture content is introduced into the upper portion 33 of the funnel 30. This material slides through the funnel and falls out the lower funnel margin 36 where it impinges upon and is deflected by a finger 40 carried within the annular bottom 13 of the test chamber 11. This finger 40 comprises a cylindrical mediate portion 41 formed of a material comprising one of the two test chamber electrodes, and a conical top 42, the tip 43 of which is aligned with the axis A of the funnel 30 and cylindrical test chamber 11. This grain flow deflecting action encourages even distribution and random mixing of the grain particles within the test chamber, and provides a uniformly dense, evenly distributed, fully representative sample in the test cell 11 for moisture testing. When the device is used with known grains, the process of fully filling the test cell and uniformly packing the test sample will provide moisture data readings of accuracy sufficient for many uses.

As the material flow rises within the test cell, the flow covers a bottom test chamber cylindrical wall 45 comprising the other of the two electrodes. In the illustrated embodiment, an outer nonconductive lower portion of the wall 47 covers this interior electrode 45 and protects it from damage which might be encountered during use.

Additional sample grain material introduced into the funnel 30 continues to flow into the test chamber until sufficient material has been received within the cell to fill it to a level providing a top material cover layer or covering R as shown especially in FIG. 2. Additionally added material will simply pile or back up within the lower portion 34 of the funnel 30. When stored in this location, this material in the funnel 30 will have little or no effect upon the dielectric constant of the material located within and near the coaxial electrodes 45 and 41. That test material sample in the test cell, however, will always be of a predetermined amount and configuration. This constant sample configuration equalizes electrode-end fringe effect and other factors from test sample to test sample. Thus the test sample material configuration will have little or no effect upon the signal issued by the electrical circuit and the data displayed on the data display 23. The tested material can be poured from the tester 10 by simply tipping it; material then runs out a pour spout 37.

When the operator has filled the tester 10 to a level which clearly covers the bottom margin 36 of the funnel device 30, he presses the actuator switch 20 to energize the electrical circuit (including the temperature compensator) and readout or display 23. To this end, a switch finger 51 abuts an extension 52 of an electrical contact 53, and moves this contact 53 into a closed position against a second contact 54, thereby completing the circuit energization.

With reference to FIG. 3, there is shown a schematic diagram of an electronic circuit which may be utilized in accordance with the principles of the present invention. The circuit of FIG. 3 comprises a fixed-frequency or "reference" oscillator 110 comprising an oscillator transistor 111 and its associated circuitry. The circuitry of FIG. 3 also includes a variable-inductance coil 112 for calibrating the circuit initially when the device of the invention is manufactured and, if necessary, for recalibration from time to time throughout the life of the device. The output of oscillator transistor 111 is applied to a first counter-decoder stage 121 of a three-stage decade counter-display unit 120 by means of a coupling capacitor 113 and a NOR gate 114. The reference oscillator signal is applied to the "clock enable" input terminal 2 of the first counter-decoder stage 121 of counter-display unit 120, as hereinafter discussed in greater detail.

The circuit of FIG. 3 also includes a variable frequency or "test" oscillator 130 which comprises a pair of oscillator transistors 131 and 132. The variable frequency oscillator 130 also includes means for adjusting the "empty-chamber" frequency of the oscillator which comprises a variable-inductance coil 133 and a variable capacitor 134, both of which are connected in parallel with a capacitance that has a value which is determined primarily by the series combination of the capacitor 135 and the coaxial capacitor formed by coaxial electrodes 41 and 45 of the test chamber 11, as described above. Moreover, the value of capacitor 135 may be selected to produce the desired frequency-readout characteristic (e.g., a direct readout of percent of moisture content as a linear function of the changes in oscillator frequency) for the particular type of grain being tested. Similar to variable-inductance coil 112 of reference oscillator 110, the variable-inductance coil 133 and the variable capacitor 134 of test oscillator 130 are adjusted initially at the factory with test chamber 11 being empty, so that the frequency of variable frequency oscillator 130 may be calibrated to a standard frequency which has a predetermined relationship with respect to the reference frequency. Moreover, an additional capacitor 136 physically located within the test chamber 11 and having a predetermined temperature coefficient may be provided in parallel with the tuning circuitry of test oscillator 130 to provide automatic temperature compensation. If the frequency of the test oscillator tends to increase with an increase in temperature, for example, a capacitor having a negative temperature coefficient would be used to compensate so that readings made when the ambient temperature is above 25° Centigrade are decreased in value and those made below 25° Centigrade are increased, with the amount of increase or decrease in value being determined empirically.

The output signal of variable frequency or test oscillator 130 is applied to twelve stages of a commercially available 14-stage divider circuit 140 by means of a NOR gate 141 and a diode 142. Although any suitable 12-stage divider may be utilized for divider 140, a well-known integrated circuit made by RCA Corporation, for example, and known as a "CD4020, 14-stage ripple-carry binary counter-divider" has been found particularly well adapted for use in the illustrated embodiment of the invention. With this circuit, input pulses from test frequency oscillator 130 are applied to the input terminal 10 of the divider 140 and the output pulses of the 11th stage ($Q_{11}$) are available at an output terminal 15 of divider 140 for application to the "clock" terminal 1 of the decade counter-decoder 121 of the counter-display unit 120. Decade counter-decoder 121 corresponds to the least significant digit of counter-display unit 120, which is the tenths digit in the embodiment of the invention illustrated in FIG. 3. The output of the 12th stage ($Q_{12}$) of divider 140 is returned (via diode 143) to input terminal 10 to lock or "clamp" divider 140 to thus terminate the count. Thus, one output pulse at output terminal 15 is produced for each $2^{10}$ input pulses (i.e. 1024 pulses) applied to input terminal 10, and the duration of this pulse is the length of time it takes for the test oscillator to generate an additional $2^{10}$ pulses. The output pulses at terminal 15 of divider 140 thus effectively gate counter-display unit 120. Consequently, the higher the frequency of the test oscillator, the lower or shorter is the time duration of the control pulse from divider 140, and vice versa.

The counter-display unit 120, as shown in the embodiment of the invention illustrated in FIG. 3, comprises three decade counters-decoders (seven-segment) 121, 122 and 123 such as SSL4426 manufactured by Solid State Scientific Inc. Respectively associated with these counter-decoders 121, 122 and 123 are current-limiting resistor networks 121a, 122a and 123a, along with seven-segment display units 121b, 122b and 123b, each display unit having its seven segments labeled a through g in the customary fashion and displaying the tenths, units and tens digits, respectively. Display units 121b, 122b and 123b are located behind the display screen 23 of FIG. 1. Of course, any number of stages may be employed, depending upon the particular application of the invention.

When actuator switch 20 is pressed, the voltage V supplied by a battery source 150 (here comprising the battery 16) is applied to the various portions of the circuit where indicated by the reference character V to initiate operation of the circuit. The battery voltage is simultaneously applied to the input of a pair of NOR gates 151 and 152 which operate as a monostable multivibrator or "one-shot" to generate a reset pulse that is applied to the reset terminal of divider 140 as well as to each of the counter-decoders 121, 122 and 123 so that all four of these circuits are reset to the zero count. At the end of the reset pulse, divider 140 begins its count. NOR gates 151 and 152, as well as NOR gates 114 and 141, may be of any suitable type; however, one integrated circuit particularly adapted for use in the illustrated embodiment of the invention is a "CD4001, quadruple two-input NOR gate" manufactured by RCA Corporation, for example. The CD4001 IC is manufactured in complementary metal-oxide semiconductor (CMOS) form and has a very high input impedance and high noise immunity.

By applying the output signal from reference oscillator 110 to the "clock" enable terminal 1 of the first counter-decoder stage 121 of display circuit 120, and simultaneously applying the output signal from test oscillator 130 (as divided by divider 140) to the "clock" terminal 1 of counter-decoder 121, the length of time that the counter is permitted to count the reference oscillator signal is effectively controlled by the frequency of the test oscillator to thus generate a digital representation of the moisture content of the material in test chamber 11 which is displayed by seven-segment display units 121b, 122b and 123b.

We claim:

1. A moisture tester for grain and the like comprising a walled test chamber including an inclined pour spout and an inclined conical distributor funnel affixed upon and extending into the chamber of the chamber top, and spaced apart electrodes forming an electrical capacitor at the chamber bottom, the electrodes being located so that the dielectric constant of the capacitor is modified in accordance with the dielectric constant of the test material sample due to moisture therein, an electrical circuit including the capacitor for generating a signal which varies systematically in accordance with the capacitor dielectric constant, the funnel distributor extending into the test chamber interior but spaced apart from the test chamber walls for uniformly distributing the material which comprises the sample introduced into the test chamber and thereby minimizing corresponding variations in the sensed test material dielectric constant the pour spout being defined in part by an inclined wall extending from the chamber at a point above the electrodes and below the funnel in a direction substantially parallel to the distributor funnel to encourage a rapid, uncongested pour-out of test sample material when the test has been completed, and conical means having a tip aligned with the funnel means axis to encourage uniform deflection, flow and packing of test material into the test chamber.

2. A moisture tester according to claim 1 including finger means affixed to a test chamber bottom wall, supporting said conical means and being aligned with the funnel means lower margin so as to encourage uniform deflection, flow and packing of test material into the test chamber.

3. A moisture tester according to claim 1 wherein said distributor means includes funnel means affixed to the test chamber and having a lower margin located at a fixed position relative to the test chamber, whereby test material introduced into the funnel means flow through the funnel means into the test chamber and fills the test chamber with only a predetermined volume of material, any additional test material introduced into the funnel means being stored in the funnel means without substantially affecting the dielectric constant of the test chamber capacitor.

4. A moisture tester according to claim 1 including manually operable electrical circuit switch means for energizing the electrical circuit when the moisture tester operator visually determines that the requisite amount of test material is present in the test chamber.

5. A moisture tester according to claim 4 including handle means affixed to the test chamber exterior and associated with said switch means to permit the moisture tester to be held and the electrical circuit actuated by one hand.

6. A moisture tester according to claim 1 wherein said spaced apart electrodes are at least two, at least one electrode comprising a test chamber interior wall, and another electrode comprising finger means spaced apart from the wall electrode means, and being aligned with the volume limit means for deflecting test material introduced into the test chamber through the volume limit means uniformly about the test chamber.

* * * * *